United States Patent [19]
Stroosnijder et al.

[11] Patent Number: 5,916,811
[45] Date of Patent: Jun. 29, 1999

[54] METHOD AND APPARATUS FOR MEASURING SPALLING OF A PROTECTIVE SURFACE

[75] Inventors: Marinus Freder Stroosnijder, Monvalle; Giovanni Michele Macchi, Gavirate, both of Italy

[73] Assignee: European Economic Community, Plateau du Kirchberg, Luxembourg

[21] Appl. No.: 08/591,478
[22] PCT Filed: Jul. 12, 1994
[86] PCT No.: PCT/EP94/02302
  § 371 Date: Jan. 11, 1996
  § 102(e) Date: Jan. 11, 1996
[87] PCT Pub. No.: WO95/02811
  PCT Pub. Date: Jan. 26, 1995

[30] Foreign Application Priority Data

Jul. 14, 1993 [GB] United Kingdom .................... 9314596

[51] Int. Cl.⁶ ..................................................... G01N 33/20
[52] U.S. Cl. .................................. 436/5; 436/56; 422/202
[58] Field of Search .................................. 436/5, 56, 171, 436/173; 422/198, 202

[56] References Cited

U.S. PATENT DOCUMENTS

| | | |
|---|---|---|
| 4,984,381 | 1/1991 | Seifert . |
| 5,457,054 | 10/1995 | Geisinger et al. ...................... 436/901 |
| 5,476,794 | 12/1995 | O'Brian et al. ........................ 436/901 |

OTHER PUBLICATIONS

Asher, *Materials Science and Engineering*, 88, 1987, 143–150.
Wortman, *Materials Science and Engineering*, A121, 1989, 22–27.
Hill, *Mechanical Engineering*, 94, Feb. 2, 1972, 22–27.
Asher et al. (1988) *Industrial Lubrication and Tribology*, 40, 4–7.
Lowell et al. (1991) *Oxidation of Metals*, 36(1/2), 81–112.
Probst and Lowell (1988) *Journal of Metals*, 18–21.
Raman and Gnanamoorthy (1992) *Materials at High Temperatures*, 10(3), 171–176.
Schneider and Blossfeld (1988) *Society of Automotive Engineers Technical Paper*, Series No. 880672, pp. 6.1257–6.1267.
Wortman et al. (1989) *Materials Science and Engineering*, A121, 433–440.
Stroosnijder et al. (1992) *Advanced Techniques for Surface Engineering*, 335–358.

*Primary Examiner*—Lyle A. Alexander
*Attorney, Agent, or Firm*—Bacon & Thomas, PLLC

[57] ABSTRACT

The present invention relates to a method and apparatus for quantitative determination of the level of spalling of a protective surface coating as a result of repetitive heating and cooling. The method comprises introducing at least one radionuclide into the protective coating of an article, alternately heating and cooling the article for a predetermined number of heating and cooling cycles, collecting the spalled particles and measuring the radioactivity thereof. The apparatus comprises a chamber for receiving the coated article, means for heating the chamber or the article and a spall collector. The spall collector is characterized in having means for immobilizing any spalled coating particles and in being so adapted that the level of radioactivity of any spalled particles can be measured by a γ-spectrometer.

18 Claims, 3 Drawing Sheets

METHOD AND APPARATUS FOR MEASURING SPALLING OF A PROTECTIVE SURFACE

The invention relates to a method of determining the level of spallation of protective surface layers or coatings from an article, such as an engine component for example, as a result of repetitive heating and cooling. The invention also relates to an apparatus suitable for use in the above-mentioned method.

In view of the desirability of providing components for various engineering applications which have improved wear resistance and corrosion resistance, much attention has been focussed in recent years on the provision of protective surface coatings for such components. There are a variety of coatings currently available which reduce attack on the component material by aggressive reactive species such as oxygen, sulphur, carbon, nitrogen, halogens or sodium and/or reduce corrosive damage which results from exposure to high temperatures.

One of the simplest forms of protective coating is an oxide scale which naturally forms on many metal alloys as a result of exposure to air or other oxidising media especially at high temperatures. A scale such as $Cr_2O_3$, $Al_2O_3$ or $SiO_2$ isolates the bare alloy from the environment and thereby slows down further corrosive attack. Other known coatings include those based on aluminium, in particular a simple aluminide applied by an aluminizing process or a modified aluminide in which the aluminium is combined with another element such as chromium, platinum or palladium or a more complex metal overlay coating of the general formula MCrAlY where M is another metallic element. Protective coatings based on ceramic materials have also been developed, based particularly on zirconia.

These latter coatings are useful in high temperature applications and form a part of the known thermal barrier coatings which consist of an MCrAlY underlay or "bond" coat and a zirconia overlay.

Apart from the above, protective surfaces can also be generated on a substrate by exposure of the surface to a high energy beam such as high energy ions, an electron beam or a laser beam.

Regardless of the type of coating, protective layers have, to a variable degree, the tendancy to flake off or spall from the coated article over time when the article is subjected to high temperatures and particularly when subjected to repeated temperature cycles, as would normally be the case with an engine component for example.

To determine the resistance to spalling of any particular coating under thermal cycling a coated article or specimen must be subjected to repeated heating and cooling cycles and the loss of coating due to spalling measured at various time intervals during the test. Such cyclic testing has been described by Singh Raman and Gnanamoorthy in Materials at High Temperatures 10 No 3 1992, 171–176, Probst and Lowell in Journal of Metals, October 1988, 18–21, Lowell et al in Oxidation of Metals 36 Nos 1/2 1991, 81–111 and by Wortman et al in Materials Science and Engineering A121 (1989), 433–440.

In the first three of the above-mentioned reports the amount of spalling is evaluated by determining the weight change (generally the specific weight change defined as weight change per unit of surface area) at various time intervals during the test e.g. after 10, 20 or 50 thermal cycles. Such weight change values can be compared with weight change in tests of similar duration at constant temperature without temperature cycles which give an indication of the effect due to high temperature exposure e.g. corrosion. However results obtained in this way can be misleading. For example, although spalling might result in weight loss, corrosion will usually result in weight gain due to the uptake of species from the environment. Therefore the relationship between weight change and material loss, the actual variable one wants to measure, can be very complicated. In addition the response to exposure of a spalled area may be different to that of an intact area and the effect of exposure at low temperature during the temperature cycle may not be negligible. Other complications arise when samples are not uniform, for example they have a coating on only one side or the coating on other sides is slightly different or there are geometrical irregularities. In such circumstances the amount of spalled material can be roughly estimated by optical determination of the spalled area, as described in the article by Wortman et al mentioned above, or by cross-sectional determination. However such methods are highly inaccurate and/or laborious and lead only to a rough quantitative ranking of materials performance.

As a solution to the above problems the present inventors have developed a new technique for determining material loss of protective surface due to spalling which involves the use of radionuclides. The method allows easy assessment of the performance of any particular protective coating during thermal cycling.

There exists a technique called thin layer activation which is described by Asher et al in Industrial Lubrication and Tribology 40 1988, 4–7 and by Schneider et al in Society of Automotive Engineers Technical Paper Series No 880672, 1988. Thin layer activation has been used to determine the rate of wear of engine components such as piston rings. In the technique radionuclides are induced within a very thin surface layer of the component by bombarding with energetic particles. Thereafter the level of radioactivity of the component may be measured in situ and its change with time recorded as an indicator of surface wear.

However the thin layer activation technique has been applied mainly to surface wear of a component and the problems of spalling of special protective coatings due to repetitive thermal cycling has not been addressed.

Thus in accordance with the present invention a method for quantative determination of the level of spalling of a protective surface coating as a result of repetitive heating and cooling of a coated or partially coated article comprises the steps of:

introducing at least one radionuclide into the whole or a portion of the protective surface coating of said coated article, (b) alternately heating and cooling said article or a portion thereof for a pre-determined number of heating and cooling cycles, (c) collecting any spalled particles in a collecting means and (d) measuring the radioactivity emitted from said collected spalled particles.

A preferred method of creating the radionuclide or radionuclides in a protective surface coating is to expose a coated article to a beam of charged particles e.g. $^1H$, $^2H$, $^3He$, $^4He$, or heavy ions from for example, a cyclotron or linear accelerator. Alternatively the radionuclide can be generated by applying a neutron beam to the article.

It will be appreciated that where the protective coating is a naturally forming surface oxide the introduction of the radionuclide into the coating may be achieved by exposing the bare surface of the article to a beam of charged particles or neutrons and as the coating forms it will automatically include the radionuclide.

In collecting the spalled particles for measurement of radioactivity (γ rays) after exposure of the article to thermal cycling, it is desirable to immobilize the particles so they remain in more or less the same position. This prevents uncontrolled loss of the radioactive material which may be a safety hazard and prevents the spalled particles from changing place which might lead to inaccuracy in the radioactivity measurements depending on the geometric conditions in the γ-spectrometer.

One way in which such immobilization can be effected is to include in the spall collector a substance such as paraffin wax which can be melted by slight heating and then solidifies when cooled so embedding and immobilizing the spalled radioactive particles. As an alternative to the wax there may be used certain low melting point metals, fats or materials capable for forming gels for immobilizing the particles.

It is necessary to measure the radioactivity of the spalled particles and so obtain an indication of material lost from the coated article, at intervals after pre-determined numbers of heating and cooling cycles. This could be after 2, 10, 20, 50 or even 2000 cycles for example. A typical thermal cycle might comprise heating the coated article to 1000° C., maintaining it at 1000° C. for 1 hour, cooling the article to 50° C. and maintaining at 50° C. for 10 minutes.

The method of the invention may be used for the assessment of any sort of special protective coating such as those described in the introduction and further can be applied whether the substrate under the coating is a metal or metal alloy or is another material such as a ceramic.

For the types of radionuclides induced in the coating layer a γ-spectrometer is a suitable instrument for measuring the radioactivity in the spalled particles.

A particular advantage of the method of the present invention is that much greater sensitivity can be achieved in measuring the radioactivity of spalled debris as opposed to measuring loss of radioactivity from an article. For example, in a typical case of direct component monitoring the maximum accuracy of any measurement will be $10^{-3}$ of the total measured. activity. Thus, the sensitivity will be 0.1 $\mu$m in the case of a 100 $\mu$m thick activated layer. However, if the activity of spalled material debris collected in accordance with the present invention is measured, the sensitivity is significantly higher and is limited essentially by the natural background radiation. The sensitivity may be increased even more if the detector and measurement sample are placed in a lead shield so reducing the background radiation.

In accordance with a second aspect of the invention there is provided an apparatus for testing the level of spalling of a protective surface coating as a result of repetitive heating and cooling of a coated or partially coated article where the coating has had introduced therein at least one radionuclide.

The apparatus comprises a chamber for receipt of the coated article, a means for heating said chamber and/or said article and a spall collector disposed at the bottom of said chamber and detachable therefrom and is characterised in that the spall collector comprises means for immobilizing any spalled coating particles and in that said collector is so adapted that the level of radioactivity of any spalled particles can be measured by a γ-spectrometer.

Preferably, the heating means is adapted to heat said chamber and/or said article independently of the spall collector.

The means provided in the spall collector for immobilizing the spalled particles may comprise an independent heating system and optionally a cooling system. Thus when said collector includes a material such as paraffin wax as aforesaid, the spall collector heating means can melt the paraffin and then subsequently cool it to solidify it, so embedding and immobilizing the spalled particles.

The chamber of the apparatus preferably has two zones, one for heating the coated article and one for cooling the article. The cooling zone may have a separate cooling means. The coated article may then be moved, by suitable means provided, between one zone and the other in a succession of heating and cooling cycles. During these cycles any radioactive spalled material falls down into the spall collector at the bottom of the chamber.

As an alternative to the above, instead of moving the article between the two zones, the heating means may move to different positions in the chamber or the heating means may simply be switched on and off or its heating capacity regulated. In such a case the coated article remains in situ during the thermal cycling.

The invention will now be described by way of example with reference to the accompanying drawings in which:

BRIEF DESCRIPTION OF THE DRAWINGS

FIG. 1 shows one possible embodiment of the apparatus of the invention which comprises a chamber which is an elongate quartz tube 2. The tube 2 is surrounded on its upper part by a furnace in the form of a circular jacket 4 for heating the tube. The temperature of the tube is measured by a thermocouple 5 and subsequently regulated by a control system. The lower end of the tube 2 is surrounded by cooling coils 6. The bottom of tube 2 is open and engages with the spall collector 8. The spall collector 8 includes an area for receiving the spalled particles 10 as well as a cooling jacket 12 and a peltier element 14.

Figure 1:
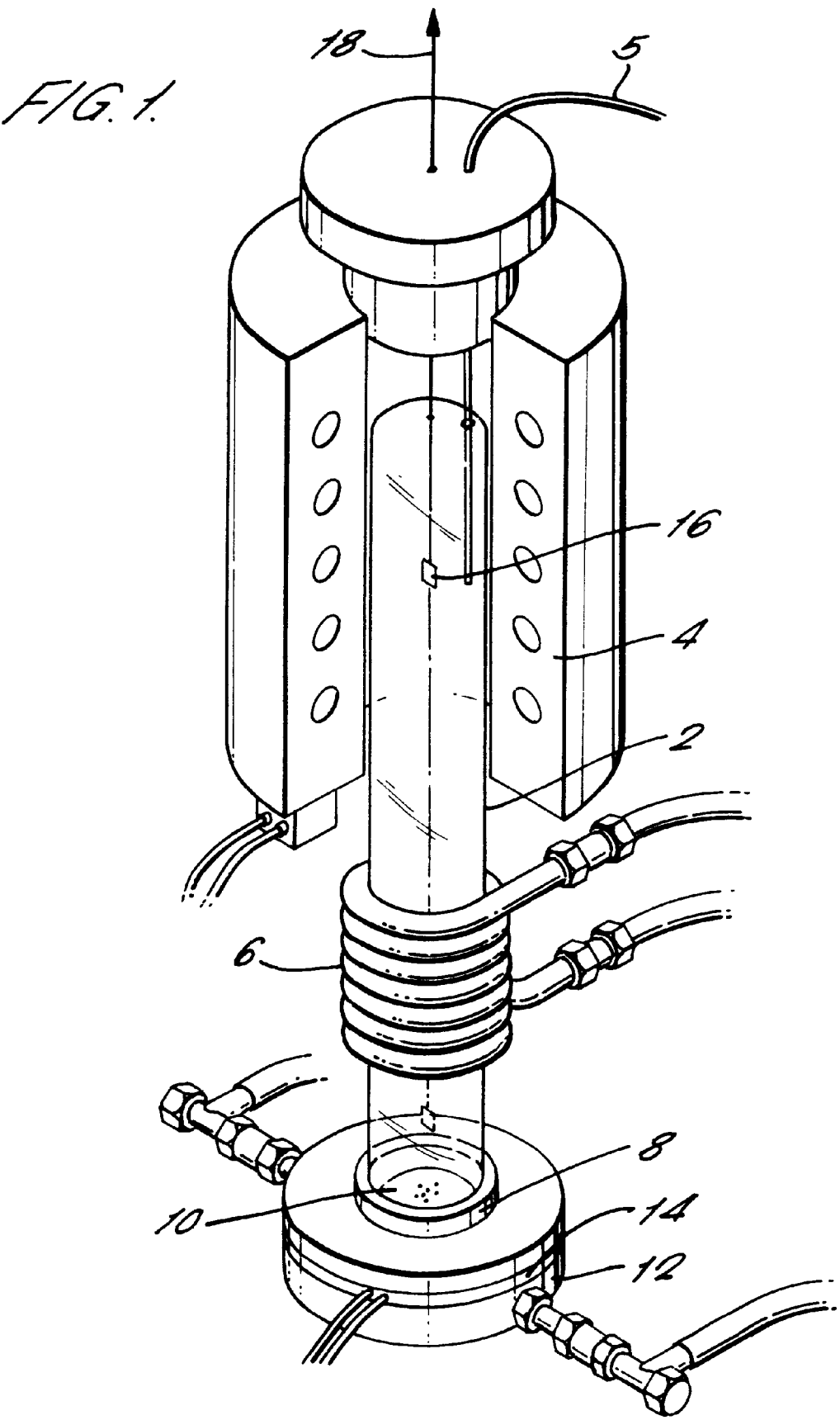
FIG. 1 is a side view, partly in section of an apparatus in accordance with the invention.

The specimen 16 is introduced into the tube 2 and is attached to a pull-cord 18. To carry out a test the furnace 4 heats the upper part of the tube 2 with the specimen 16 in the upper position. When the specimen has been held at a constant temperature for an appropriate period it is lowered into the cooling zone of the tube 2, cooled and held at a lower constant temperature. Thereafter it is raised to the heating zone of the tube 2 and the cycle is started again and repeated for as many thermal cycles as are required.

Before any spalled particles in the spall collector 8 are tested for γ radiation, the peltier element 14 heats the collector to melt the paraffin wax or other meltable substance and the cooling jacket 12 and the peltier element 14 then cool the collector to solidify the paraffin and embed the spalled particles.

The apparatus described above was used to carry out spallation behaviour tests on various coating materials in accordance with the following examples.

EXAMPLE 1

The influence of bond coat on the spallation of thermal barrier coatings was investigated by carrying out a spallation behaviour test for two coatings as follows:

(1) Zirconia based ceramic coating (2) Thermal barrier coating i.e. zirconia based ceramic coating with metallic bond coat.

Activation of samples was performed on a specific area of one side only by exposure of the specimens to a beam of protons with an energy of 18 MeV coming from a cylotron. The total coating thicknesses were about 300 µm. The depth of activation was about 500 µm. Each thermal cycle consisted of heating to 1000° C. and maintaining this temperature for 10 minutes and then cooling to about 30° C. and maintaining at this temperature for 10 minutes. Various radioisotopes were used as an indication of material loss e.g. $^{89}$Zr and $^{92}$Nb.

Figure 2:
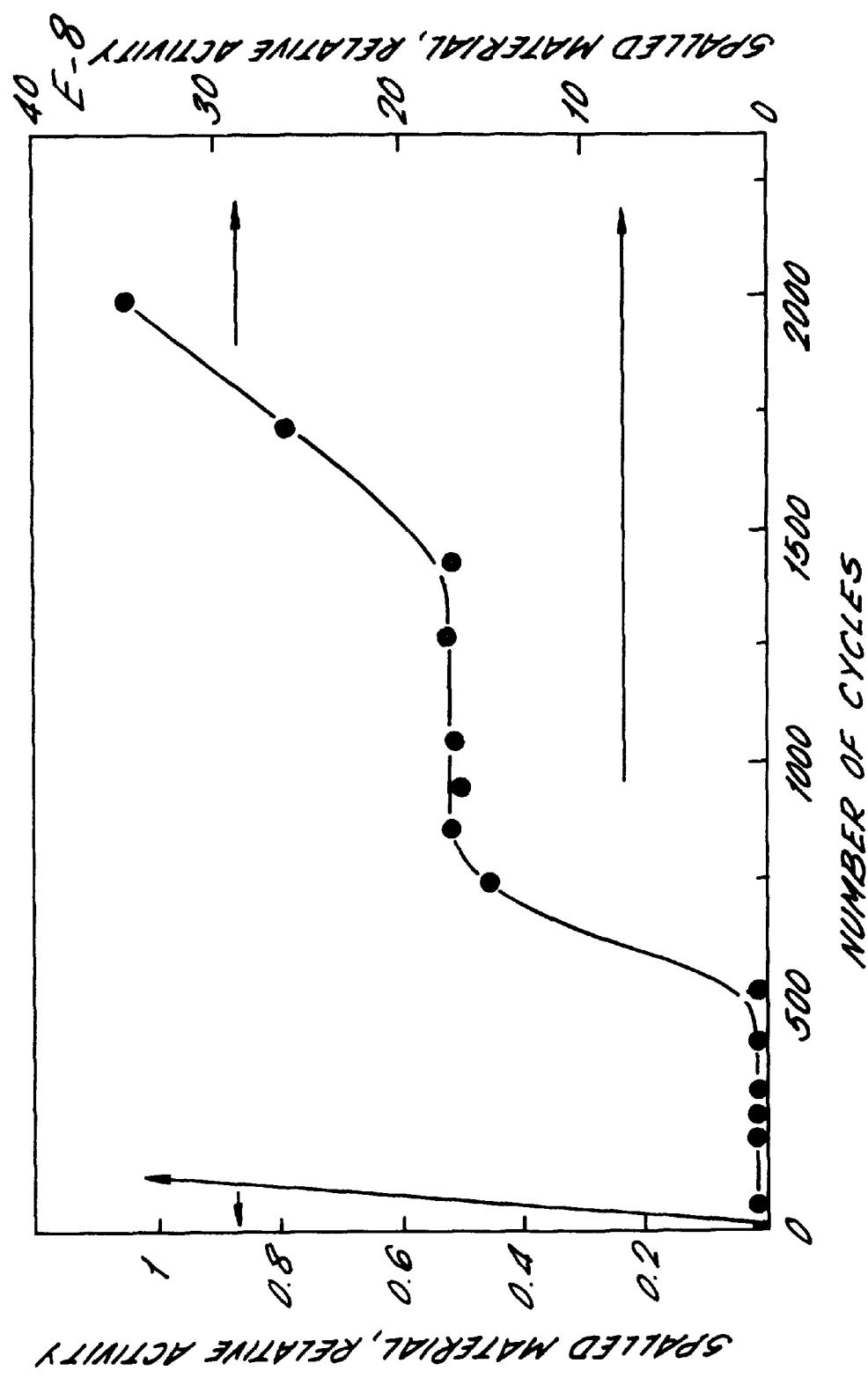
FIG. 2 is a graph showing the spallation behaviour as a function of number of thermal cycles of two different zirconia based coatings with and without a metallic bond coat on a metallic substrate and FIG. 3 is a graph showing the spallation behaviour due to thermal cycling of an oxide layer which is forming on chromium due to reaction with air at high temperature.

The results of the experiment are shown in FIG. 2 where relative activity of the spalled material is plotted against the number of thermal cycles. The spallation is expressed as relative activity i.e. ratio of spalled material/sample corrected for natural decay of the radioisotopes. On the right hand axis 20 E-8 corresponds to an amount of spallation of zirconia per unit surface area of 30 ng/cm$^2$. As can readily be seen from the figure the zirconia without bond coat (▲—▲) failed totally after 6 cycles while the known thermal barrier coating, the zirconia with metallic bond coat (•—•) had a dramatically increased resistance to spalling and did not fail until at least 2000 cyles had been completed.

EXAMPLE 2

In this example the spallation behaviour due to thermal cycling of an oxide layer which forms on powder metallurgical chromium due to exposure to air at high temperatures was investigated.

Activation of the samples was performed on a specific area of one side only. The depth of activation was about 100 µm. The isotope $^{51}$Cr was used as an indication of the material lost. The thermal cycle carried out consisted of heating to 1000° C. or 800° C. and maintaining at this temperature for 1 hour and then cooling to about 30° C. and marinating at this temperature for 12 minutes.

Figure 3:
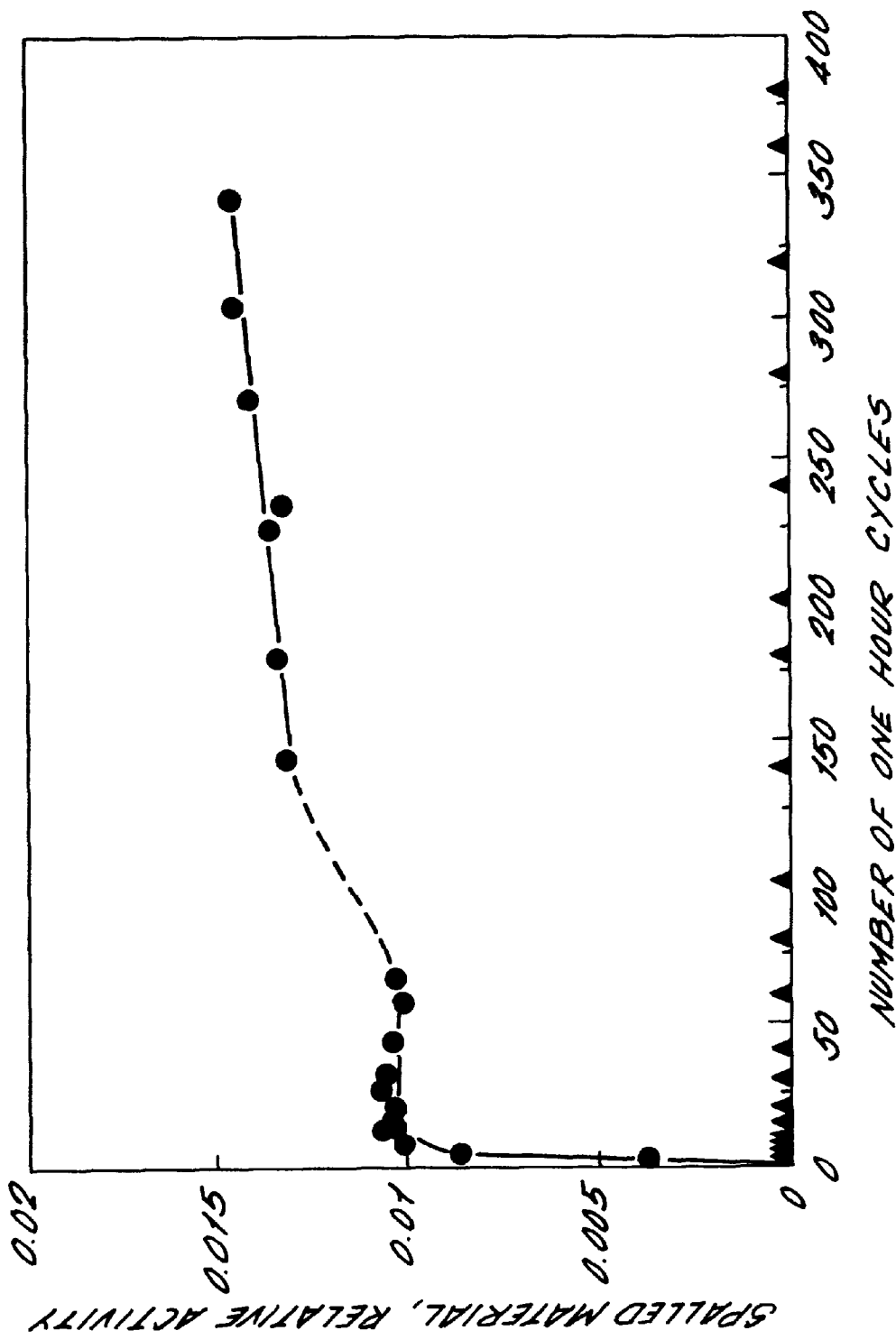

The results of this experiment are shown in FIG. 3 where the relative activity of the spalled material is plotted against the number of 1 hour cycles (•—•T=1000° C.,▲—▲T=800° C.). As can be seen the oxide layer is rather susceptible to spalling at 1000° C. as a result of thermal cycling, especially in the first 10 cycles. 0.01 on the vertical axis corresponds to a loss of Cr of 0.7 mg/cm$^2$. Contrarily, a maximum temperature of 800° C. in the thermal cycle led to no detectable spalling until at least 400 cycles.

The method and apparatus of the invention can be used to determine the level of spalling of any coating as a result of exposure to thermal cycling with much greater accuracy that has hitherto been possible. It represents a significant improvement over the known methods based on measurement of weight change, optical determination or cross-sectional determination.

We claim:

1. A method for quantitative determination of the level of spalling of a protective surface coating as a result of repetitive heating and cooling of a coated or partially coated article which method comprises the steps of:
    (a) introducing at least one radionuclide into the whole or a portion of the protective surface coating of said coated article,
    (b) alternately heating and cooling said article or a portion thereof for a predetermined number of heating and cooling cycles,
    (c) collecting any spalled particles in a collecting means, and
    (d) measuring the radioactivity emitted from said collected spalled particles, and
    (e) using the measure of radioactivity in the spalled particles obtained in step (d) as an indication of the level of spalling from the coated article at intervals after predetermined numbers of heating and cooling cycles, wherein prior to step (d) the collected spalled particles are immobilized in a thin layer of a solid substance which can be melted by slight heating and then solidifies when cooled so embedding and immobilizing the spalled radioactive particles.

2. A method as claimed in claim 1 wherein the at least one radionuclide is created in the protective surface coating by exposure of said coating to a beam of charged particles from a cyclotron or linear accelerator or by exposure to a neutron beam.

3. A method as claimed in claim 1 wherein the at least one radionuclide is created in the protective surface coating by exposing the bare surface of the article to a beam of charged particles or neutrons and then allowing the protective coating to form by surface oxidation of the article.

4. A method as claimed in claim 1 wherein a single heating and cooling cycle consists of heating said coated article to 1000° C., maintaining the article at 1000° C. for 1 hour, cooling the article to 50° C. and maintaining the article at 50° C. for 10 minutes.

5. A method as claimed in claim 1 wherein said article is of a metallic, ceramic or polymeric material.

6. A method as claimed in claim 1 wherein said protective surface coating is an aluminide or modified aluminide consisting of aluminium in combination with one or more of platinum, chromium or palladium, a metallic overlay coating of the MCrAlY type where M is another metal, an oxide such as $Cr_2O_3$, $Al_2O_3$ or $SiO_2$, a ceramic coating based on zirconia or a thermal barrier coating comprising a bond layer of an MCrAlY material and a zirconia overlay.

7. A method as claimed in claim 1 wherein said protective surface coating is one generated by exposing the uncoated surface of the article to a high energy ion beam, an electron beam or a laser beam.

8. A method as claimed in claim 1 wherein said coated article undergoes at least 2 heating and cooling cycles.

9. A method as claimed in claim 8 wherein said coated article undergoes at least 50 heating and cooling cycles.

10. A method as claimed in claim 1, wherein said solid substance is selected from paraffin wax, fats, low melting point materials and materials capable of forming gels.

11. A method as claimed in claim 10, wherein the article is a ceramic based article.

12. An apparatus for testing the level of spalling of a protective surface coating as a result of repetitive heating and cooling of a coated or partially coated article wherein said coating has had introduced therein at least one radionuclide, the apparatus comprising a chamber for receipt of said coated article, a means for heating said chamber and/or said article, and a spall collector disposed at the bottom of said chamber and detachable therefrom wherein the said heating means is adapted to heat said chamber and/or said article independently of said spall collector and said spall collector comprises means for immobilizing any spalled coating particles in a thin layer of a solid substance which can be melted by slight heating and then solidifies when cooled so embedding and immobilizing the spalled radioactive particles and is so adapted that the level of radioactivity of any spalled particles can be measured by a γ-spectrometer.

13. An apparatus as claimed in claim 12 wherein said chamber heating means is adapted to be moved to heat different areas of the chamber.

14. An apparatus as claimed in claim 12 wherein the means for immobilizing said particles in the spall collector includes a heating system independent of said chamber heating means.

15. An apparatus as claimed in claim 14 wherein the means for immobilizing said particles in the spall collector includes a heating and cooling system independent of said chamber heating means.

16. An apparatus as claimed in claim 12 wherein said chamber comprises a first zone for heating said article and a second zone for cooling said article.

17. An apparatus as claimed in claim 16 wherein said second zone includes a cooling means.

18. An apparatus as claimed in claim 16 having means for moving said article between the first and second zone.

* * * * *